(12) United States Patent
Kono

(10) Patent No.: US 12,357,268 B2
(45) Date of Patent: Jul. 15, 2025

(54) ULTRASOUND ENDOSCOPE AND METHOD OF MANUFACTURING ULTRASOUND ENDOSCOPE

(71) Applicant: OLYMPUS CORPORATION, Tokyo (JP)

(72) Inventor: Hirotoshi Kono, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 146 days.

(21) Appl. No.: 18/085,253

(22) Filed: Dec. 20, 2022

(65) Prior Publication Data
US 2023/0119963 A1 Apr. 20, 2023

Related U.S. Application Data

(63) Continuation of application No. PCT/JP2020/029858, filed on Aug. 4, 2020.

(51) Int. Cl.
*A61B 8/12* (2006.01)
*A61B 8/00* (2006.01)

(52) U.S. Cl.
CPC .............. *A61B 8/12* (2013.01); *A61B 8/4245* (2013.01); *A61B 2562/12* (2013.01)

(58) Field of Classification Search
CPC ..... A61B 8/12; A61B 8/4245; A61B 2562/12; A61B 8/445; A61B 8/4483
See application file for complete search history.

(56) References Cited

U.S. PATENT DOCUMENTS

| 2011/0218443 | A1* | 9/2011 | Sawada | ................. B06B 1/067 |
| | | | | 600/459 |
| 2018/0271490 | A1* | 9/2018 | Kitahara | ................. A61B 8/12 |
| 2019/0159755 | A1 | 5/2019 | Kitahara | |

FOREIGN PATENT DOCUMENTS

| JP | 2004209044 A | 7/2004 |
| WO | 2017/094528 A1 | 6/2017 |
| WO | 2018/025679 A1 | 2/2018 |

OTHER PUBLICATIONS

International Search Report dated Sep. 8, 2020 received in PCT/JP2020/029858.

* cited by examiner

*Primary Examiner* — Anne M Kozak
*Assistant Examiner* — Kaitlyn E Sebastian
(74) *Attorney, Agent, or Firm* — Scully, Scott, Murphy & Presser, P.C.

(57) ABSTRACT

An ultrasound endoscope includes an ultrasound transducer unit provided at a distal end of the ultrasound endoscope. The ultrasound transducer unit includes: an ultrasound transducer configured to transmit and receives an ultrasonic wave; and a housing that includes a housing portion to house the ultrasound transducer, the housing portion including a plurality of protrusions configured to position the ultrasound transducer, each protrusion being arranged to face a rear surface on an opposite side to a transceiving surface of the ultrasonic wave of the ultrasound transducer, the protrusions being arranged to be across a longitudinal axis of the housing from one another.

20 Claims, 6 Drawing Sheets

ULTRASOUND ENDOSCOPE AND METHOD OF MANUFACTURING ULTRASOUND ENDOSCOPE

CROSS-REFERENCE TO RELATED APPLICATION

This application is a continuation of International Application No. PCT/JP2020/029858, filed on Aug. 4, 2020, the entire contents of which are incorporated herein by reference.

BACKGROUND

1. Technical Field

The present disclosure relates to an ultrasound endoscope and a method of manufacturing an ultrasound endoscope.

2. Related Art

In the related art, an ultrasound endoscope in which an ultrasound transducer is arranged at a distal end of an insertion portion that is inserted into the body of a subject has been known (for example, JP-A-2004-209044). The ultrasound transducer is fixed to a housing arranged at the distal end of the insertion portion.

SUMMARY

In some embodiments, an ultrasound endoscope includes an ultrasound transducer unit provided at a distal end of the ultrasound endoscope. The ultrasound transducer unit includes: an ultrasound transducer configured to transmit and receives an ultrasonic wave; and a housing that includes a housing portion to house the ultrasound transducer, the housing portion including a plurality of protrusions configured to position the ultrasound transducer, each protrusion being arranged to face a rear surface on an opposite side to a transceiving surface of the ultrasonic wave of the ultrasound transducer, the protrusions being arranged to be across a longitudinal axis of the housing from one another.

The above and other features, advantages and technical and industrial significance of this disclosure will be better understood by reading the following detailed description of presently preferred embodiments of the disclosure, when considered in connection with the accompanying drawings.

DETAILED DESCRIPTION

Figure 1:
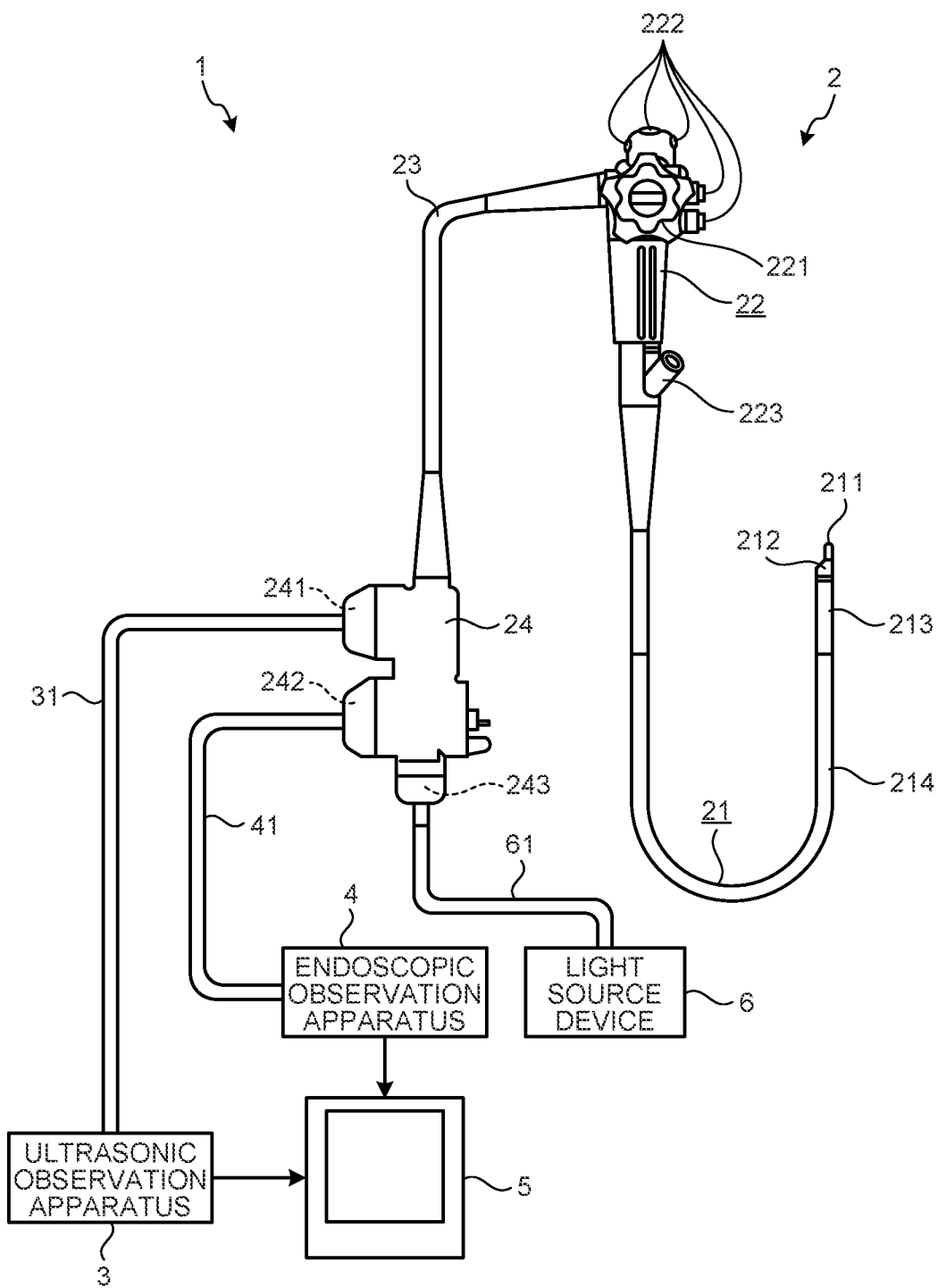
FIG. 1 is a diagram schematically illustrating an endoscope system according to an embodiment of the disclosure.

Hereinafter, an embodiment of an ultrasound endoscope according to the disclosure and a method of manufacturing the ultrasound endoscope will be explained with reference to the drawings. The embodiment is not intended to limit the disclosure. The disclosure is applicable to a general ultrasound transducer unit that includes an ultrasound transducer and a housing that holds the ultrasound transducer.

Moreover, in the drawings, identical reference symbols are assigned to identical or corresponding components appropriately. It is noted that the drawings are schematic illustration, and dimensional relationships of the respective components, ratios of the respective components, and the like can differ from an actual situation. Also among the drawings, parts in which dimensional relationships and ratios differ from one another may be included.

Embodiment

FIG. 1 is a diagram schematically illustrating an endoscope system according to an embodiment of the disclosure. An endoscope system 1 is a system that performs ultrasound diagnosis inside the body of a subject, such as human, by using an ultrasound endoscope. This endoscope system 1 includes an endoscope 2, an ultrasonic observation apparatus 3, an endoscopic observation apparatus 4, a display device 5, and a light source device 6.

The endoscope 2 is configured such that a part thereof can be inserted in to the body of a subject, and is an ultrasound endoscope that has a function of transmitting an ultrasound pulse toward a body wall inside a subject and receiving an ultrasound echo that has been reflected on the subject to output an echo signal, and a function of capturing an inside of the body of a subject and outputting an image signal. A detailed configuration of the endoscope 2 will be described later.

The ultrasonic observation apparatus 3 is electrically connected to the endoscope 2 through an ultrasonic cable 31, outputs a pulse signal to the endoscope 2 through the ultrasonic cable 31, and receives an echo signal from the endoscope 2. The ultrasonic observation apparatus 3 generates an ultrasound image by subjecting the echo signal to predetermined processing.

The endoscopic observation apparatus 4 is electrically connected to the endoscope 2 through a video cable 41, and receives an image signal from the endoscope 2 through the video cable 41. The endoscopic observation apparatus 4 generates an endoscopic image by subjecting the image signal to predetermined processing.

The display device 5 is constituted of a liquid crystal or an organic electroluminescence (EL), and displays an ultrasound image generated by the ultrasonic observation apparatus 3, an endoscopic image generated by the endoscopic observation apparatus 4, and the like.

The light source device 6 is connected to the endoscope 2 through an optical fiber cable 61, and supplies illumination light to illuminate inside the body of the subject through the optical fiber cable 61.

The endoscope 2 includes an insertion portion 21, an operating portion 22, a universal cord 23, and a connector 24. A term "distal end" described in the following signifies an end portion that is positioned on the opposite side to the side of the operating portion 22 of the insertion portion 21. Moreover, a term "proximal end" described in the following signifies an end portion that is positioned on a side (side of the operating portion 22) separating away from the distal end of the insertion portion 21.

The insertion portion 21 is a portion that is inserted in to the body of a subject. This insertion portion 21 includes an ultrasound transducer unit 211 arranged at a distal end side, a hard member 212 that is joined to the proximal end side of the ultrasound transducer unit 211, a bendable portion 213 that is joined to the proximal end side of the hard member 212 and is bendable, and a flexible tube portion 214 that is joined to the proximal end side of the bendable portion 213 and that has flexibility.

Inside the insertion portion 21, a light guide (not illustrated) that transmits illumination light supplied by the light source device 6, an image guide described later that guides an optical image inside the subject, plural signal cables that transmit various kinds of signals (for example, a signal cable 2112 described later (refer to FIG. 2) that is electrically connected to the ultrasonic cable 31 through the universal cord 23, and the like), and a tube (not illustrated) in which various kinds of treatment tools (not illustrated) are inserted are drawn through. A detailed configuration of the distal end side of the ultrasound transducer unit 211 will be described later.

The hard member 212 is a hard member that is made from a resin material, and has a substantially cylindrical shape. In the hard member 212, an objective lens to which observation light (an optical image) to generate a captured image of the inside of the subject enters, an illumination lens from which illumination light is emitted, an opening portion that lets a treatment tool and the like protrude out therethrough, and the like are arranged.

The bendable portion 213 has a cylindrical shape, and is a portion that that bends according to an operation of an operating knob 221 by a doctor or the like.

The operating portion 22 is a portion that is joined to the proximal end side of the insertion portion 21, and that accepts various kinds of operations from a doctor or the like. This operating portion 22 includes the operating knob 221 to manipulate the bendable portion 213 to be bent, and a plurality of operating members 222 to perform various operations. Moreover, in the operating portion 22, a treatment tool inlet 223 that communicates with a tube (not illustrated) arranged inside the insertion portion 21, and that is to insert various kinds of treatment tools into the tube is formed. Furthermore, inside the operating portion 22, an imaging device (not illustrated) that outputs an image signal according to an optical image of the inside of the subject, and an optical system (not illustrated) that forms an optical image guided through the image guide on the imaging device are arranged.

The universal cord 23 has one end connected to the operating portion 22, and plural signal cables to transmit various kinds of signals, an optical fiber to transmit illumination light supplied by the light source device 6, and the like are arranged.

The connector 24 is arranged on the other end of the universal cord 23. The connector 24 includes first to third connector portions 241 to 243 to which the ultrasonic cable 31, the video cable 41, and the optical fiber cable 61 are respectively connected.

Figure 2:
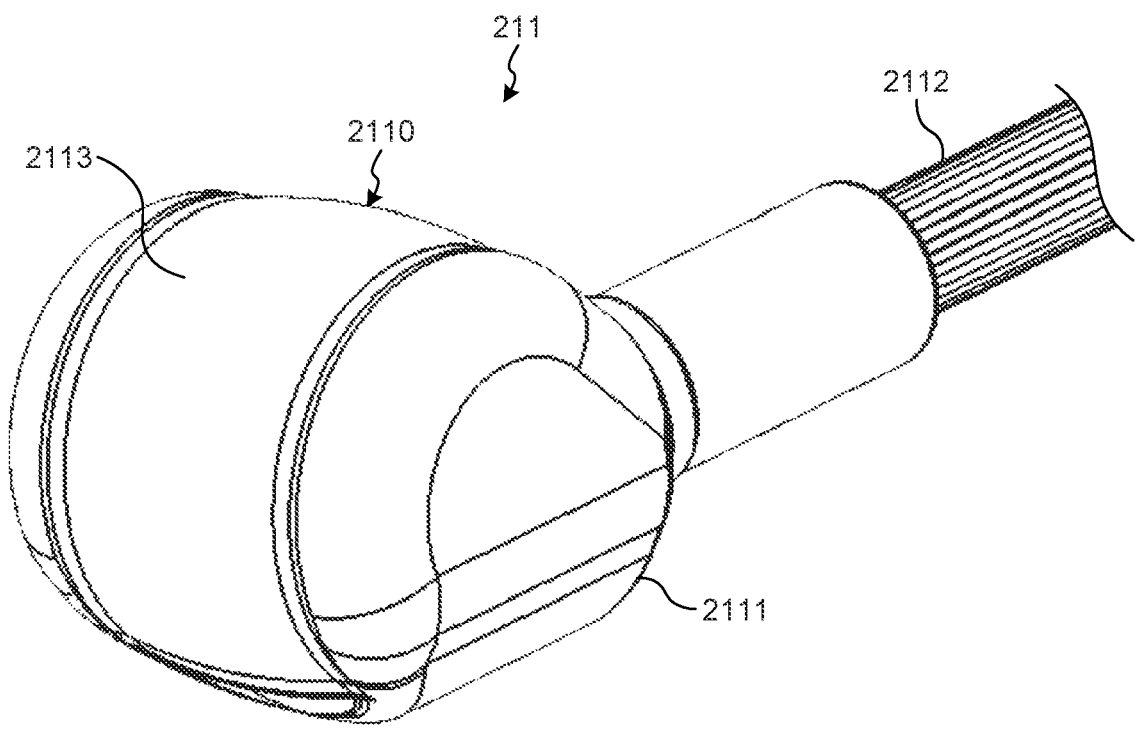
FIG. 2 is a perspective view of an ultrasound transducer unit.

FIG. 2 is a perspective view of the ultrasound transducer unit. The ultrasound transducer unit 211 includes a convex ultrasound transducer 2110, and a housing 2111 that houses the ultrasound transducer 2110. To the housing 2111, a part of the hard member 212 on the proximal end side is inserted.

Figure 3:
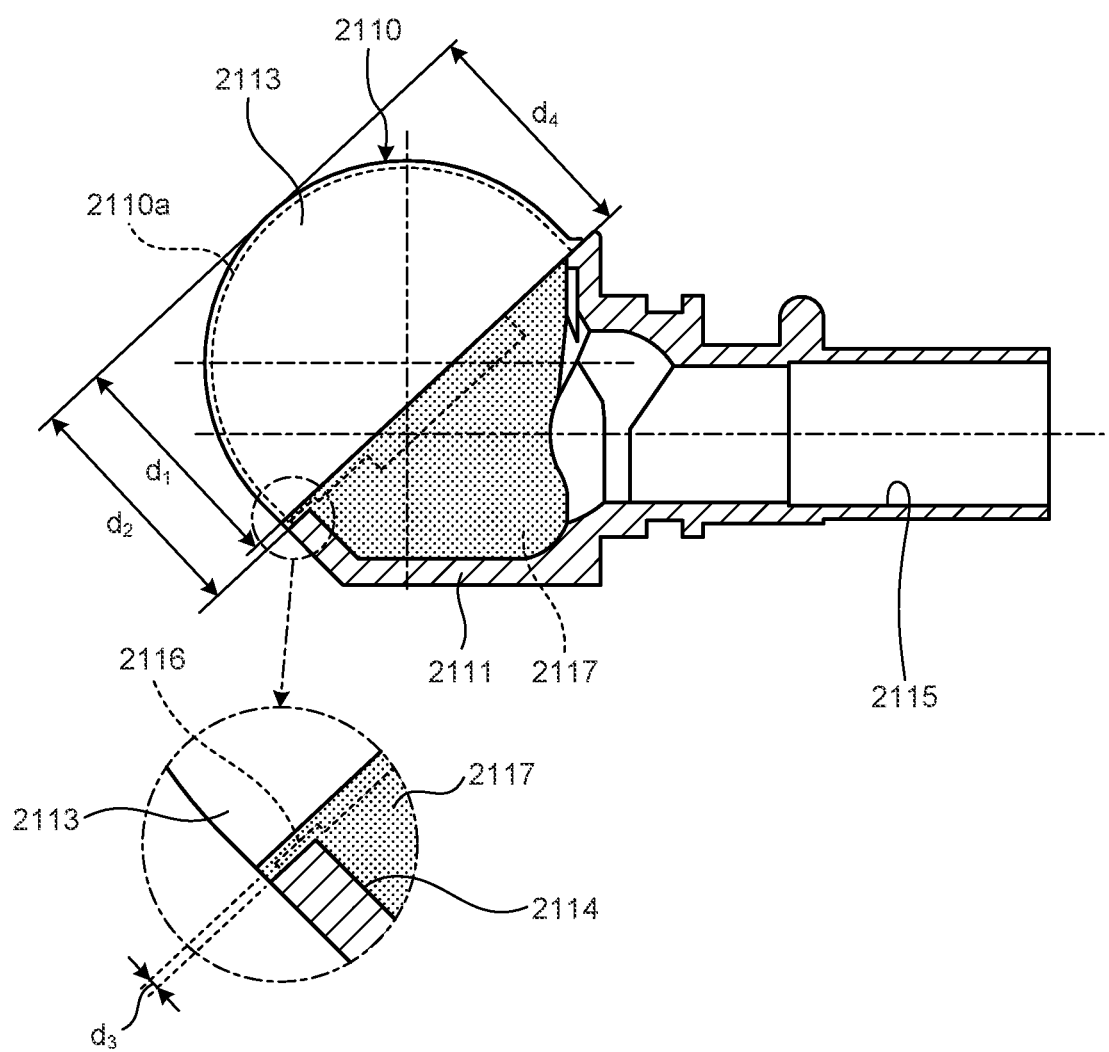
FIG. 3 is a partial cross-section of the ultrasound transducer unit illustrated in FIG. 2.

First, a configuration of the ultrasound transducer 2110 will be explained. FIG. 3 is a partial cross-section of the ultrasound transducer unit illustrated in FIG. 2. The ultrasound transducer 2110 is a convex ultrasound transducer. Moreover, to the ultrasound transducer 2110, the signal cable 2112 is connected. The ultrasound transducer 2110 receives a pulse signal from the ultrasonic observation apparatus 3 through the signal cable 2112, and transmits an echo signal based on the ultrasound echo to the ultrasonic observation apparatus 3. In the ultrasound transducer 2110, an acoustic lens is arranged, and ultrasonic waves are communicated with an external unit through this acoustic lens. The acoustic lens is formed by using a relatively soft material, such as silicon resin, polymethylpentene, epoxy resin, and polyetherimide, and a surface to transmit and receive ultrasonic waves have a convex shape or a concave shape (for example, a convex shape 2110a illustrated in FIG. 3). The acoustic lens has a function of converging ultrasonic waves emitted from the ultrasound transducer 2110, and of forming a thin beam. A cover member 2113 is arranged on the ultrasound transducer 2110, and this cover member 2113 constitutes an external surface of the ultrasound transducer 2110. The cover member 2113 is formed by using a soft resin. The cover member 2113 may be made from the same material as the acoustic lens and, for example, when the acoustic lens is formed by using silicon resin, the cover member 2113 is also formed by using silicon resin.

Figure 4:
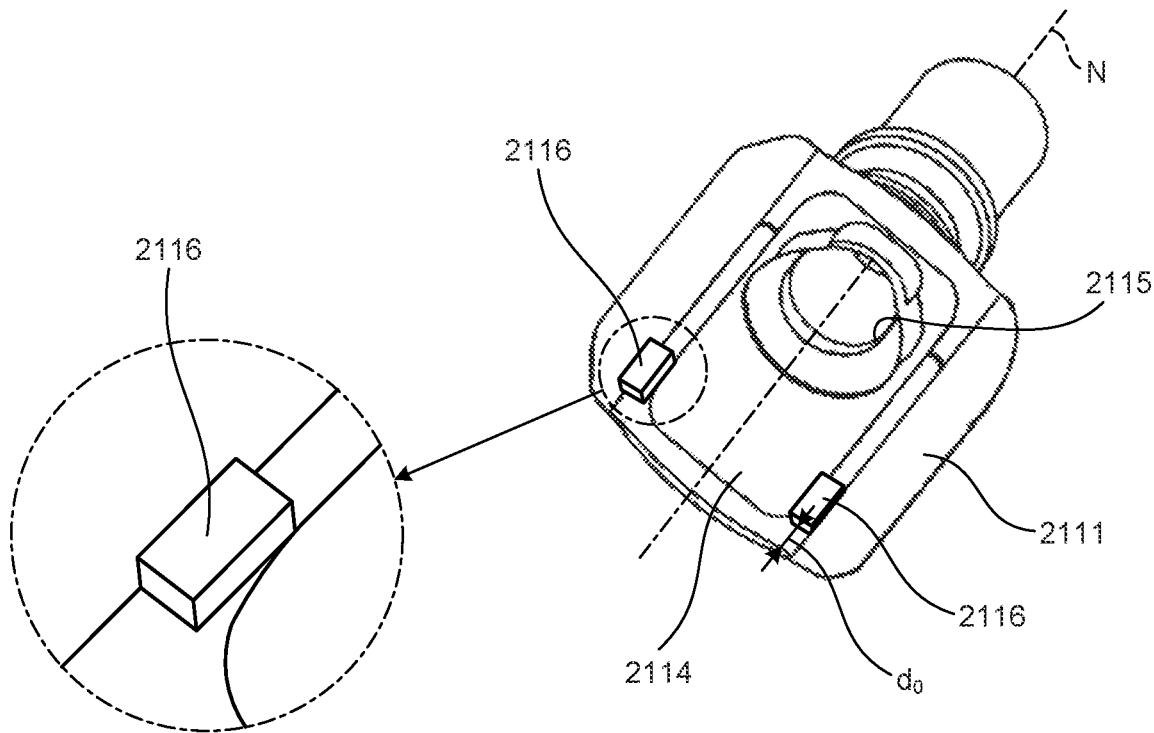
FIG. 4 is a perspective view illustrating a configuration of a housing of the ultrasound transducer unit.

Subsequently, a configuration of the housing 2111 will be explained. FIG. 4 is a perspective view illustrating a configuration of the housing of the ultrasound transducer unit. The housing 2111 has a housing portion 2114 that houses and holds the ultrasound transducer 2110. Moreover, in the housing 2111, an insertion hole 2115 in which the signal cable 2112 is inserted is formed. Furthermore, in the housing 2111, two protrusions 2116 are formed on the distal end side of the housing portion 2114 (refer to FIGS. 3, 4). The protrusions 2116 are arranged at positions across a longitudinal axis N of the housing 2111 from one another. The protrusion 2116 is formed at a position apart from the distal end of the housing 2111 by predetermined distance do (>0) (refer to FIG. 4). The distance do is set according to connection thickness of the ultrasound transducer 2110 and the housing 2111 at the distal end. In the protrusion 2116, a surface facing the ultrasound transducer 2110 has a flat plane.

The ultrasound transducer 2110 is fixed to the housing 2111 with an adhesive 2117 put inside the housing portion 2114. In this fixed state, the distal end side of the ultrasound transducer 2110 is fixed to the housing 2111 through the adhesive 2117, and the proximal end side is in contact with an opening end of the housing portion 2114.

A distance $d_1$ from a head portion of the ultrasound transducer 2110 to an end portion on a side facing the housing 2111 of the ultrasound transducer 2110 on the distal end side of the ultrasound transducer unit 211 is shorter than a distance $d_2$ from the head of the ultrasound transducer 2110 to the opening end of the housing 2111 on the distal end side of the ultrasound transducer unit 211 (refer to FIG. 3). Furthermore, a difference between the distance $d_2$ and the distance $d_1$ is equal to or larger than a protrusion height $d_3$ of the protrusion 2116. FIG. 3 illustrates an example of $d_2 - d_1 > d_3$.

Moreover, the distance $d_1$ is shorter than a distance $d_4$ from the head portion of the ultrasound transducer 2110 to the opening end of the housing 2111 on the proximal end of the ultrasound transducer unit 211.

Next, a method of manufacturing the ultrasound transducer will be explained. In the present embodiment, a method of manufacturing the ultrasound transducer unit 211 will be explained, referring to FIG. 5 to FIG. 8. FIG. 5 to FIG. 8 are diagrams explaining the method of manufacturing the ultrasound transducer unit.

Figure 5:
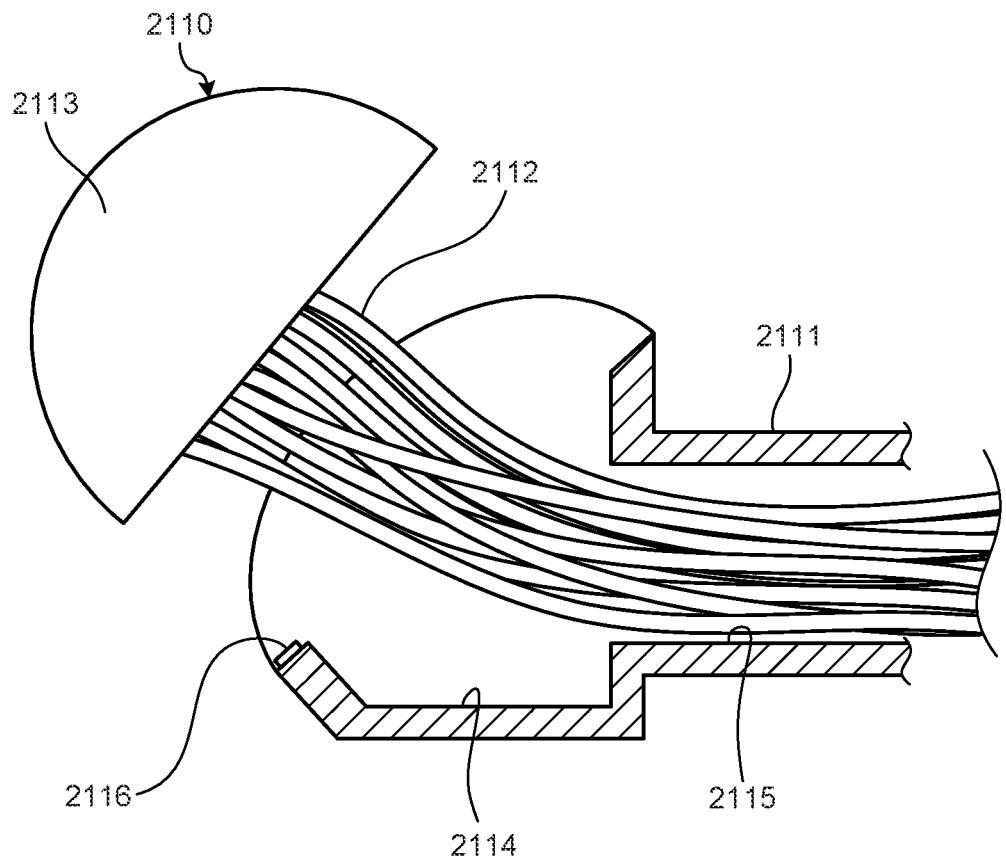
FIG. 5 is a diagram (Part 1) explaining a method of manufacturing the ultrasound transducer unit.

First, the signal cable 2112 is inserted in the insertion hole 2115 of the housing 2111, and after insertion, one end of the signal cable 2112 is connected to the ultrasound transducer 2110 (refer to FIG. 5).

Figure 6:
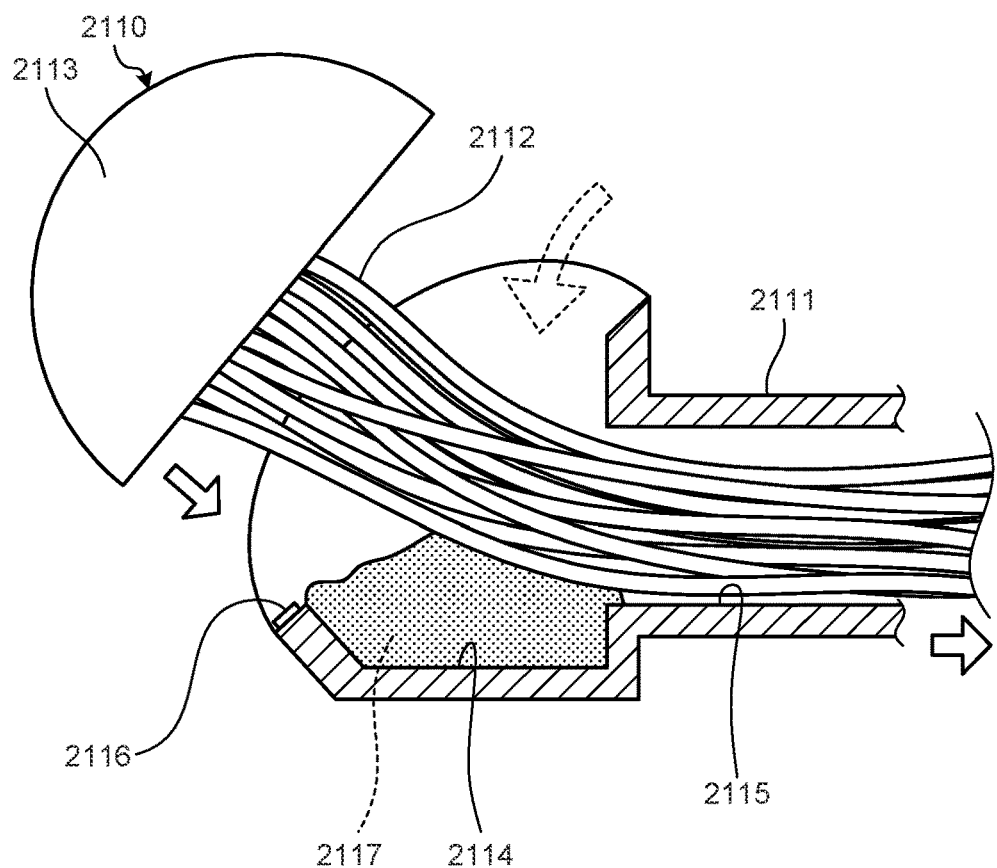
FIG. 6 is a diagram (Part 2) explaining the method of manufacturing the ultrasound transducer unit.

After connecting the ultrasound transducer 2110 to the signal cable 2112, the ultrasound transducer 2110 is drawn toward the housing 2111 by sliding the housing 2111 toward the ultrasound transducer 2110 (refer to FIG. 6). Moreover, at this time, the adhesive 2117 is poured in the housing portion 2114. At this time, the adhesive 2117 is in a liquid form. The adhesive in a liquid form includes one in a transformable state, such as gel.

Figure 7:
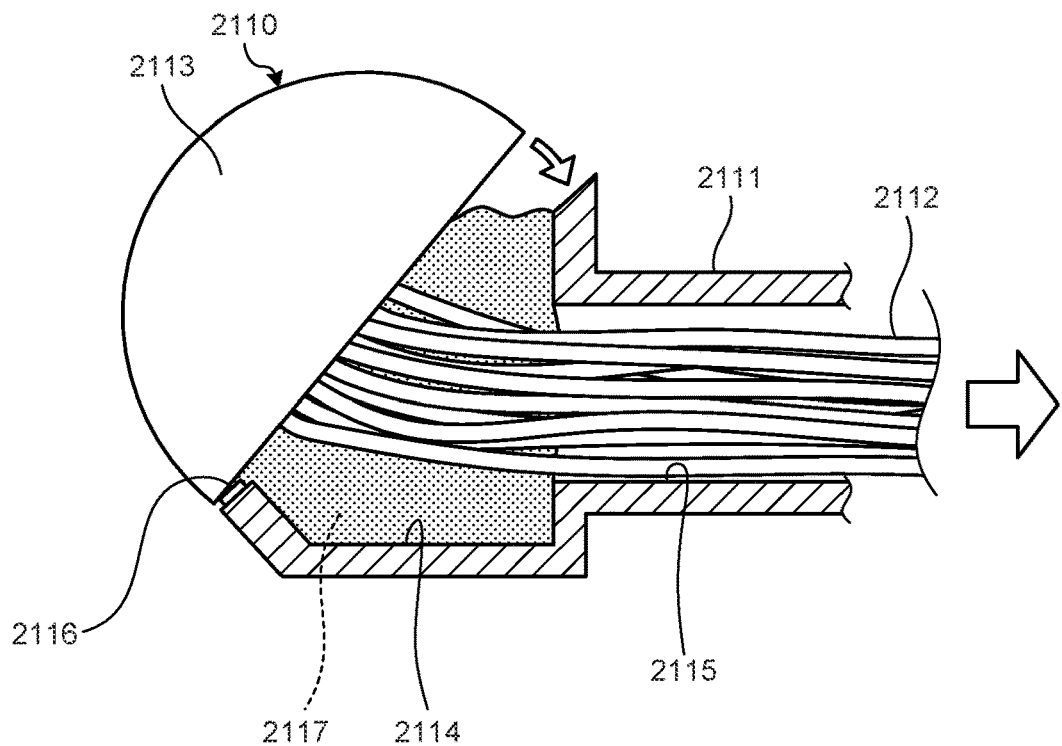
FIG. 7 is a diagram (Part 3) explaining the method of manufacturing the ultrasound transducer unit.
Figure 8:
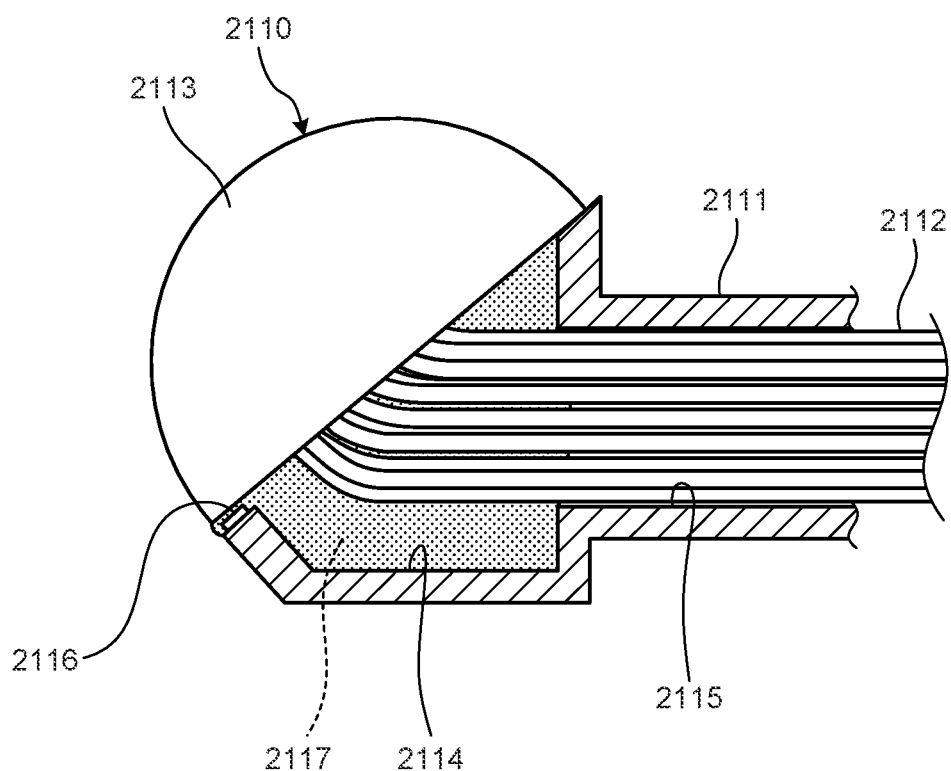
FIG. 8 is a diagram (Part 4) explaining the method of manufacturing the ultrasound transducer unit.

Thereafter, the distal end side of the ultrasound transducer 2110 drawn toward the housing 2111 is brought to abut on the protrusions 2116 (refer to FIG. 7). At this time, the proximal end side of the ultrasound transducer 2110 is not abutting on the housing 2111, but is in a separated state.

In the state in which the ultrasound transducer 2110 abuts on the protrusions 2116, the proximal end side of the ultrasound transducer 2110 is brought to abut on the housing 2111. At this time, the adhesive 2117 overflowing from the housing portion 2114 flows out to the outside of the housing 2111. In this situation, the adhesive 2117 may enter a gap between the protrusion 2116 and the ultrasound transducer 2110 formed when the distal end side of the ultrasound transducer 2110 comes apart from the protrusion 2116.

Thereafter, by curing the adhesive 2117, the ultrasound transducer 2110 is fixed to the housing 2111. Examples of the adhesive 2117 include one that is cured by predetermined temperature.

By assembling the hard member 212 after assembling the ultrasound transducer unit 211 by the flow explained above, the insertion portion 21 is formed. By assembling respective parts, as connecting this insertion portion 21 with the operating portion 22, or the like, the endoscope 2 is manufactured.

The timing of pouring the adhesive 2117 may be before abutting the ultrasound transducer 2110 on the protrusion 2116, or may be after abutting.

In the embodiment of the disclosure explained above, the protrusion 2116 is arranged in the housing portion 2114 of the housing 2111, and at the time of assembly, one end side is positioned by abutting the ultrasound transducer 2110 on the protrusion 2116, and an excessive portion of the adhesive 2117 is discharged out from the proximal end side, to fix the ultrasound transducer 2110 to the housing 2111. According to the present embodiment, when assembling the ultrasound transducer 2110 having an unstable shape, it is possible to position and fix the ultrasound transducer 2110 with respect to the housing 2111, and consequently, it is possible to achieve the fixing position of the ultrasound transducer with respect to the housing.

Moreover, according to the present embodiment, by adjusting the height of the protrusion 2116, connection thickness of the ultrasound transducer 2110 and the housing 2111 on the distal end side can be adjusted.

Furthermore, according to the present embodiment, just by providing the protrusion 2116 in the housing 2111, a constant positioning effect can be obtained, and, individual variability in a scanning direction of ultrasonic wave caused by misalignment at manufacturing can be suppressed while suppressing increase in size of the ultrasound transducer 2110 and the housing 2111 because an additional part for positioning or the like is not necessary.

The ultrasound transducer 2110 for an ultrasound endoscope is covered with resin on its entire periphery, to ensure watertightness and electric insulation property. This resin is formed by using the same soft material as the acoustic lens, and is apt to be deformed. Conventionally, to suppress the deformation of this resin, a measures in which the ultrasound transducer 2110 is not pushed hard against the housing 2111 by making the adhesive thick has been taken. In the present embodiment, by providing the protrusion 2116 in the housing 2111, positioning is enabled while minimally suppressing the deformation of the resin portion described above. A term "positioning" herein means to determine a position of the ultrasound transducer 2110 in a direction inclining at a predetermined angle with respect to the longitudinal direction of the endoscope 2. That is, according to the present embodiment, it is possible to stabilize an inclination angle of the ultrasound transducer 2110 in the endoscope 2.

Modification

Figure 9:
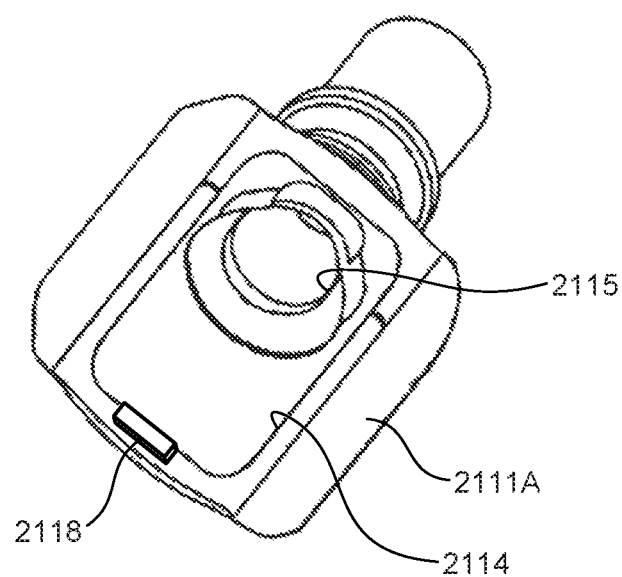
FIG. 9 is a perspective view illustrating a configuration of a housing of an ultrasound transducer unit according to a modification.

Next, a modification of the embodiment will be explained, referring to FIG. 9. FIG. 9 is a perspective view illustrating a configuration of a housing of an ultrasound transducer unit according to the modification. A configuration of an endoscope system according to a first modification is same as that of the endoscope system 1 described above except that the protrusion 2116 in the housing 2111 is modified and, therefore, explanation thereof will be omitted. Hereinafter, a configuration different from the embodiment will be explained.

In a housing 2111A according to the present modification, a protrusion 2118 is arranged on the distal end side of the housing portion 2114 and at a central portion through which the longitudinal axis N of the housing 2111A passes. The protrusion height of the protrusion has the same relationship as the protrusion height $d_3$ with respect to the housing 2111A and the ultrasound transducer 2110.

Moreover, the protrusion 2118 has a function of fixing the ultrasound transducer 2110 to the housing 2111 similar to the protrusion 2116 described above, and contributes to positioning of the ultrasound transducer 2110. The method of manufacturing other than that is the same as that of the embodiment described above.

In the modification explained above, the protrusion 2118 is arranged in the housing portion 2114 of the housing 2111A, and at the time of assembly, one end side is positioned by abutting the ultrasound transducer 2110 on the protrusion 2118, and an excessive portion of the adhesive 2117 is discharged out from the proximal end side, to fix the ultrasound transducer 2110 to the housing 2111A. According to the present embodiment, when assembling the ultrasound transducer 2110 having an unstable shape, it is possible to position and fix the ultrasound transducer 2110 with respect to the housing 2111A, and consequently, it is possible to achieve the fixing position of the ultrasound transducer with respect to the housing.

In the embodiment and the modification described above, the protrusions 2116, 2118 have been explained as an example as a positioning portion to position the ultrasound transducer 2110 with respect to the housing 2111, but as long as it is configured to be capable of positioning, it is not limited to protrusion. Moreover, the protrusions 2116, 2118 have been explained to have a flat plane on a surface facing the ultrasound transducer 2110, but may have a tapered distal end shape or a spherical surface.

The embodiment to implement the disclosure have so far been explained, but the disclosure is not to be limited to the embodiment described above. The disclosure can include various embodiments not described herein and the like. In the embodiment described above, an external ultrasound probe that irradiates an ultrasonic wave from a body surface of a subject may be adopted as the ultrasound probe. The external ultrasound probe is usually used when observing abdominal organs (liver, gallbladder, urinary bladder), breasts (particularly, mammary gland), and thyroid gland.

An ultrasound endoscope and a method of manufacturing an ultrasound endoscope according to the disclosure explained above are useful for determining a fixing position of an ultrasound transducer with respect to a housing.

According to the disclosure, it is possible to achieve a fixing position of an ultrasound transducer with respect to a housing.

Additional advantages and modifications will readily occur to those skilled in the art. Therefore, the disclosure in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An ultrasound endoscope comprising:
    a housing having a first opening and including a plurality of protrusions disposed on a first rim defining the first opening; and
    an ultrasound transducer cover configured to house an ultrasound transducer within a cavity having a second opening, the ultrasound transducer configured to transmit and receive an ultrasonic wave, the ultrasound transducer cover including a first surface exposed from the housing and a second peripheral surface defining the second opening, the second peripheral surface covering the first rim;
    wherein the second peripheral surface abuts the plurality of protrusions.

2. The ultrasound endoscope according to claim 1, wherein the plurality of protrusions are disposed at positions apart from a distal end of the housing by a predetermined distance.

3. The ultrasound endoscope according to claim 1, wherein the plurality of protrusions each comprise a flat surface facing the second peripheral surface.

4. The ultrasound endoscope according to claim 1, wherein an external surface of the ultrasound transducer cover is resin.

5. The ultrasound endoscope according to claim 4, wherein the resin is made from a material same as a material of an acoustic lens.

6. The ultrasound endoscope according to claim 5, wherein the resin is silicon resin.

7. The ultrasound endoscope according to claim 1, further comprising an adhesive disposed in the housing for fixing a signal cable from the ultrasound transducer in the housing.

8. The ultrasound endoscope according to claim 1, wherein the ultrasound transducer is a convex ultrasound transducer.

9. The ultrasound endoscope according to claim 1, wherein:
    the housing includes a first side surface,
    the ultrasound transducer cover includes a second side surface located between the second peripheral surface and a surface configured to transmit and receive the ultrasonic wave,
    the first side surface faces the second side surface, and
    the first rim is adjacent to the first side surface.

10. The ultrasound endoscope according to claim 1, wherein:
    the housing comprises a proximal portion, the proximal portion being tubular and extending in a longitudinal direction; and
    the first rim is inclined relative to the longitudinal direction.

11. The ultrasound endoscope according to claim 1, wherein the first rim faces the second peripheral surface.

12. The ultrasound endoscope according to claim 1, wherein the plurality of protrusions are located on a distal end of the first rim.

13. The ultrasound endoscope according to claim 12, wherein the plurality of protrusions abut a distal end of the second peripheral surface, the distal end of the second peripheral surface is spaced apart from the distal end of the first rim.

14. The ultrasound endoscope according to claim 1, wherein the plurality of protrusions abut a distal end of the second peripheral surface, and the first rim abuts a proximal end of the second peripheral surface.

15. The ultrasound endoscope according to claim 1, wherein the housing includes a bottom surface and a protruding surface, the protruding surface protrudes from the bottom surface in a protruding direction, the first rim is disposed on a distal end of the protruding surface in the protruding direction.

16. The ultrasound endoscope according to claim 1, wherein
    the ultrasound transducer cover includes:
        a front surface opposed to the second peripheral surface, and
        a side surface located between the front surface and the second peripheral surface,
    the housing covers the side surface and the second peripheral surface.

17. A method of manufacturing an ultrasound endoscope, the method comprising:
    introducing an adhesive into a housing having a first opening and a first rim defining the first opening;
    abutting a distal end of a second peripheral surface of an ultrasound transducer cover on a plurality of protrusions arranged on the first rim, the second peripheral surface defining a second opening of a cavity housing an ultrasound transducer, the ultrasound transducer cover having a first surface though which the ultrasound transducer is configured to transmit an ultrasonic wave;
    while the adhesive is in a liquid form and while maintaining the abutting of the distal end of the second peripheral surface on the plurality of protrusions, moving a proximal end of the second peripheral surface to cover the first rim; and
    curing the adhesive.

18. The method according to claim 17, wherein the first rim faces the second peripheral surface.

19. The method according to claim 17, wherein the proximal end of the second peripheral surface abuts the first rim.

20. The method according to claim 17, wherein
the ultrasound transducer cover includes a side surface located between the second peripheral surface and a surface configured to transmit and receive the ultrasonic wave,
the housing covers the side surface and the second peripheral surface.

* * * * *